United States Patent [19]

Hiramoto et al.

[11] Patent Number: 4,458,685
[45] Date of Patent: Jul. 10, 1984

[54] TRANSCUTANEOUS CARBON DIOXIDE MEASUREMENT ELECTRODE ASSEMBLY

[75] Inventors: Junichi Hiramoto; Tamotsu Fukai; Shinichi Ohkawa, all of Osaka, Japan

[73] Assignee: Sumitomo Electric Industries, Ltd., Osaka, Japan

[21] Appl. No.: 258,628

[22] Filed: Apr. 29, 1981

[30] Foreign Application Priority Data

Apr. 29, 1980 [JP] Japan ................. 55-57597

[51] Int. Cl.³ .............................. A61B 5/00
[52] U.S. Cl. .................... 128/635; 204/403; 204/420; 204/433
[58] Field of Search ........... 128/635; 204/195 B, 204/195 P, 195 G, 195 M, 403, 420, 433

[56] References Cited

U.S. PATENT DOCUMENTS

| | | | |
|---|---|---|---|
| 3,436,329 | 4/1969 | Kahn et al. | 128/635 X |
| 3,853,731 | 12/1974 | Gray et al. | 204/195 G |
| 3,933,612 | 1/1976 | Fischer et al. | 204/195 G |
| 4,133,735 | 1/1979 | Afromowitz et al. | 204/195 G |
| 4,197,853 | 4/1980 | Parker | 128/635 |

OTHER PUBLICATIONS

Ahn et al., "Development of a Miniature pH Glass . . . ", MBE, vol. 13, No. 3, pp. 450-456, May 1975.

Primary Examiner—Lee S. Cohen

[57] ABSTRACT

A transcutaneous gas measuring assembly is described in which a glass electrode is formed by a body of highly insulating material and a bottom by a glass membrane. The membrane is provided with a conductive layer on the inner surface thereof and a preamplifier is disposed within the glass electrode and electrically connected to the conductive layer. A reference electrode is disposed around the glass electrode. All of the above form a measuring portion of the gas measuring assembly.

1 Claim, 4 Drawing Figures

TRANSCUTANEOUS CARBON DIOXIDE MEASUREMENT ELECTRODE ASSEMBLY

FIELD OF THE INVENTION

The present invention relates to an electrode assembly for transcutaneously measuring carbon dioxide concentration (or partial pressure) in the tissue or in the blood of the patient.

Detecting $CO_2$ concentrations in the blood is extremely important for clinical tests for studying breathing and metabolism functions and for determine the approximate pH values of the blood of the patient.

BACKGROUND OF THE INVENTION

In the conventional art, there is known a method of direct measurement by withdrawal of the blood from the patient, particularly the blood from an artery, for detecting $CO_2$ concentration in the blood. This method was, however, not suitable for continuous measurement and caused pains to the patient.

The method of transcutaneous measurement according to the present invention is different from the direct method described above. Because the present invention measures the carbon dioxide which is diffused from blood and through capillary blood vessels and skin, it does not cause any pain to the patient and is capable of continuously measuring the $CO_2$ partial pressure of the patient.

Reference is now made to the accompanying drawings wherein:

FIG. 1 is a cross sectional view showing a basic structure of a transcutaneous carbon dioxide measuring electrode assembly used in the prior art. In FIG. 1, the measuring electrode assembly has a structure in which a potential difference between an internal electrode 4 immersed in a buffer solution 3 which is enclosed in the glass electrode 2 of an insulated glass tube having the bottom of a pH responsive glass membrane and a external reference electrode 5 of silver and silver chloride is taken out by a pair of lead wires 6, 7 respectively.

In this method, the impedance of pH responsive glass membrane 2 is about $10^8$ ohm even in the case of a general electrode; it reaches from $10^9$ ohm to $10^{10}$ ohm in the case of the transcutaneous measurement electrode when a fine particle glass is used.

In view of the foregoing, it is necessary to use a preamplifier having an extremely high impedance. But when doing so, if a long lead wire connecting the glass electrode and the preamplifier is used, interfering noise is transmitted by the electrostatic and magnetic induction of the lead wire.

In FIG. 1, 9 denotes a membrane holder bonding a stretched $CO_2$ permeable polymer membrane 8. 10 denotes a skin heating membrane which provides a body contact surface and an aperture through which measuring gas is carried to said glass electrode and further provides a heater for heating the measurement portion and heat sensitive element controlling said heater to keep the measurement portion at a designated temperature and which supports the membrane holder 9 in a space between said reference electrode 5 and said skin heating member so as to exert pressure on the $CO_2$ permeable membrane 8.

FIG. 2 shows a cross section of another improved prior art type of transcutaneous $CO_2$ measurement assembly which is designed to overcome the above defects. A preamplifier 27 is placed at an upper position of the glass electrode. The preamplifier 27 is connected to the internal electrode 24 immersed in a buffer solution 23 which is enclosed in the glass electrode. The glass electrode is made of insulating tubular member 22 bonded by pH responsive glass membrane 21 so as to form its bottom.

The output terminal of the preamplifier 27 is connected to an external measurement main body which is placed apart from the electrode assembly by lead wires 28 with a low output impedance which is produced by the impedance conversion function of the preamplifier. The membrane holder 9 with a $CO_2$ permeable polymer membrane 8 and a skin heating member having heater 30 and heat sensitive element 31 are the same as those shown in FIG. 1. The skin heating member 10 exerts pressure on the $CO_2$ permeable membrane interposing electrolyte solution on the outer surface of said glass membrane 21 in the same manner as in FIG. 1. However, the improved prior art assembly as shown in FIG. 2 still has defects, more specifically in the following respects.

(1) The assembly becomes larger in size because it houses a preamplifier at an upper place of the glass electrode, and therefore it is not convenient to use the assembly for prematured and neonatal babies with small body surface.

(2) Because the lead wire from the glass electrode to the preamplifier has a high impedance, this easily takes up noises.

(3) It is required to shield the portion of the lead wire from the glass electrode to the preamplifier.

(4) When the sensor falls or is inverted by the moving of the patient, the buffer solution of the glass electrode runs out, thereby happens disconnection in the lead wire of the glass electrode.

(5) The buffer solution may happen to freeze causing the glass electrode enclosing the buffer solution to break under preservation and/or transportation in very cold climates.

(6) When the assembly is heated for transcutaneous measurement, the buffer solution may become vaporized and form dews because of the uneven temperature distribution over the glass electrode. The composition of the solution changes locally, and abnormal measurement values may appear.

(7) The buffer solution which has leaked out of the glass electrode may deteriorate insulation.

(8) The pH responsive glass membrane is easily broken.

(a) The skin heating member 10 is designed to heat a skin measurement portion of the patient and the glass electrode to maintain both at a designated temperature. Therefore, it is not sufficient to maintain the preamplifier provided outside of the glass electrode at a constant temperature. The changes in temperature of the preamplifier causes drifts in output voltage and deteriorates the measurement precision of the electrode assembly.

OUTLINE OF THE INVENTION

The conventional type measurement assembly has an extremely high impedance, thereby the input impedance of the preamplifier should also be high. Since the external measurement main body which is placed apart from the electrode assembly is connected by a long lead wire to the electrode assembly, input noise is unavoidably produced by the electrostatic and electrostatic and electromagnetic induction.

According to the present invention, the electrode assembly of the present invention has a structure wherein a preamplifier is equipped within the glass electrode, the input lead wire between a conductor layer made on the inner surface of the glass membrane and the preamplifier is extremely short, and the external measurement main body and the preamplifier is connected by a lead wire with a low output impedance of the preamplifier. Thereby the problems of noise caused by high input impedance of the preamplifier is effectively removed. As the preamplifier is equipped in the glass electrode maintained at a constant temperature, the changes in the preamplifier gains and the offset drifts according to the temperature changes are extremely reduced.

DESCRIPTION OF PREFERRED EMBODIMENTS OF THE PRESENT INVENTION

Figure 3:
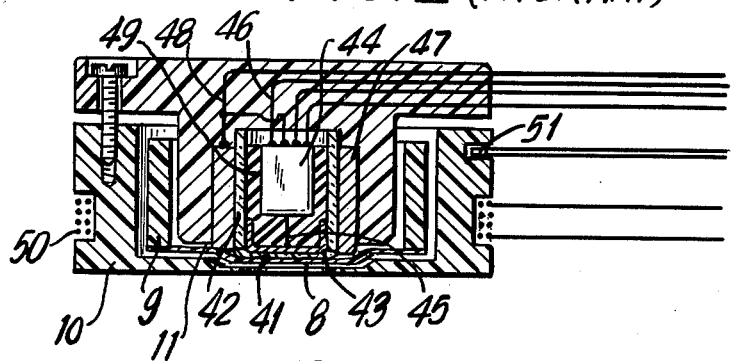
FIg. 3 shows a cross sectional view of a transcutaneous $CO_2$ measurement assembly according to the present invention.

The present invention contributes to remove the defects of the above mentioned conventional type assembly. Its structure is shown in FIG. 3.

The present invention will be explained in detail by referring to FIG. 3. A PH responsive glass membrane 41 is bonded to an insulating tubular member 42 so as to form its bottom. A conductive layer 43 is formed on the inner surface of th pH responsive glass membrane 41. A preamplifier is equipped within the tubular member 42. The electromotive force generated at the pH responsive glass membrane 41 is transmitted to the preamplifier 44 by a short lead wire 45 from the conductive layer 43.

The preamplifier delivers a low output impedance to the output lead wire which is connected to the external measurement main body.

Figure 1:
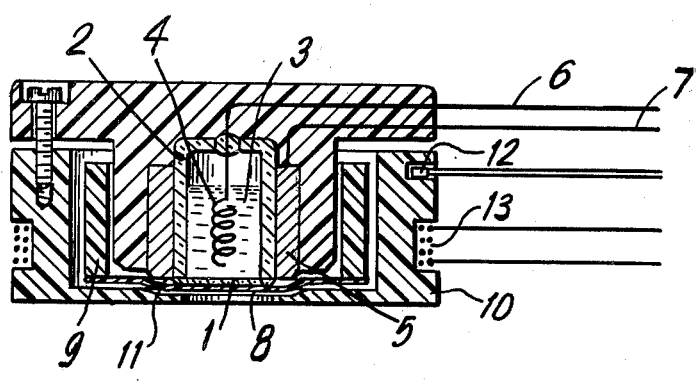
FIG. 1 shows a cross sectional view of a conventional type transcutaneous $CO_2$ measurement assembly.
Figure 2:
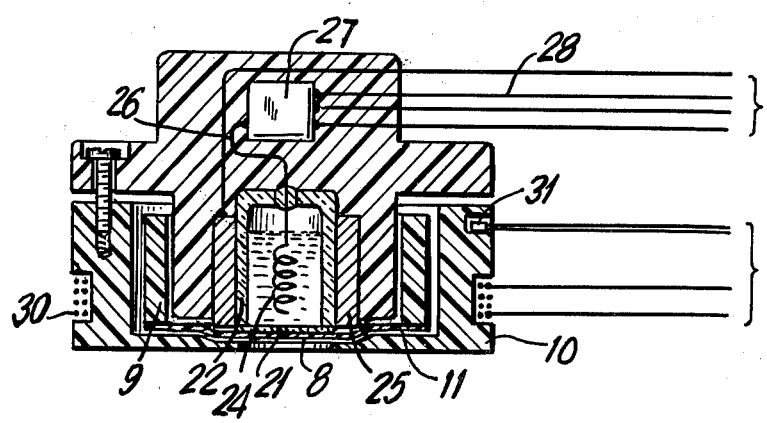
FIG. 2 shows a cross sectional view of an improved type transcutaneous $CO_2$ measurement assembly housing a preamplifier therein.

An external reference electrode 47 is so disposed as to surround the glass electrode, and the potential thereof is kept at the ground potential and taken out by lead wire 48. The heater member 10 having a heater 50 and a heat sensitive element 51 and a membrane holder 9 with a $CO_2$ permeable polymer membrane 8 are the same as shown in FIG. 1 and FIG. 2. Between the $CO_2$ permeable membrane 8 and the outer surface of the pH responsive glass membrane 41, there is interposed an electrolyte solution in contact with the exposed surface of the external reference electrode in the same way as shown in FIG. 1 and FIG. 2.

We shall now explain the present invention by referring to a concrete embodiment thereof. The pH responsive glass membrane 41 is bonded to the insulating tubular member 42 with a silicone type adhesive agent so as to form the bottom. The insulating tubular member 42 has a dimension of 6 mm outer diameter, 5 mm inner diameter and 8 mm height and is made of such a highly insulating material as epoxy resin. 70 $\mu$m of silver coating is deposited in vacuum on the inner surface of the pH responsive glass membrane 41 to form the conductive layer 43. A metallic case type MOS FET (4 mm in diameter, 4 mm in height) is used as the preamplifier 44 which is disposed in the glass electrode whose input terminal is connected with the conductive layer 43 by a very short lead wire 45 and whose output terminal is connected to the external measuring main body by the output lead wires 46.

The space 49, excluding the preamplifier and the input lead wire inside the glass electrode, is filled with silicone rubber compound of a normal temperature hardening type in order to increase the mechanical strength and improve the insulating properties of the assembly.

Figure 4:
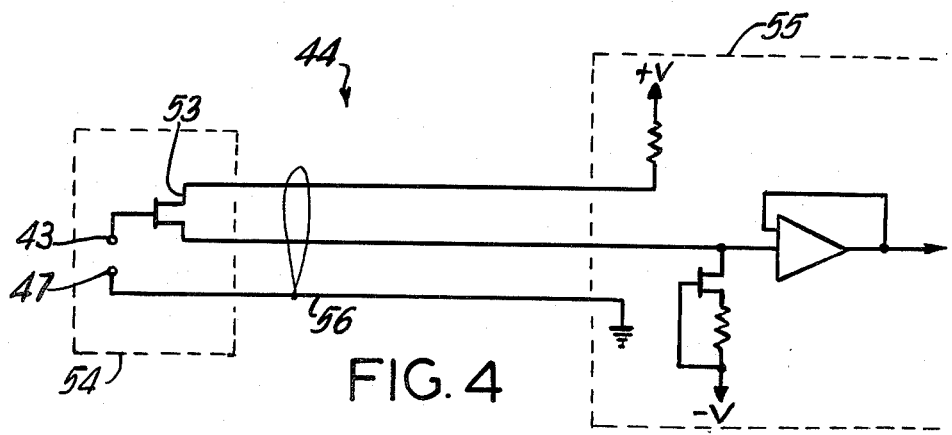
FIG. 4 shows a circuit diagram for the preamplifier.

The circuit diagram of the preamplifier 44 and its connections are shown in FIG. 1. In FIG. 4, the gate terminal of the MOS FET 53 is connected to the conductive layer 43, the output lead wires from the MOS FET which comprises the preamplifier 44 are led from the electrode assembly 54 and connected to the external measurement main body 55. The output lead wires are composed of a shielded cable 56 whose outer shielding conductor is connected to the reference electrode 47 which has the ground potential and the earth terminal of the external measurement main body 55.

Table 1 shows the results of comparison of the conventional type assembly shown in FIG. 1 (hereinafter referred to as the conventional type I), the conventional type assembly shown in FIG. 2 (hereinafter referred to as the conventional type II) and the assembly according to the present invention discussed above.

TABLE 1

| Comparison of Transcutaneous $CO_2$ Measurement Assemblies | | | |
|---|---|---|---|
| | Conventional type I | Conventional type II | Present invention type |
| Gas response sensitivity ($CO_2$ 5% 10%) | Potential change, 16 mV | Potential change, 16 mV | Potential change, 16 mV |
| Noise level | Potential change, less than 2.3 mV | Potential change, less than 0.2 mV | Potential change, less than 0.1 mV |
| Drift | Potential change, less than 0.4 mV/H | Potential change, less than 0.6 mV/H | Potential change, less than 0.1 mV/H |
| Measurement values for human (mmHg) | | | |
| 1. Neonatal (3 days old) | 30 | 31 | 32 |
| 2. Infant (3 yr. old) | Too active, measurement impossible | Too active, measurement impossible | 35 |
| 3. Adult (healthy) | 41 | 40 | 41 |

TABLE 1-continued

| Comparison of Transcutaneous $CO_2$ Measurement Assemblies | | | |
|---|---|---|---|
| | Conventional type I | Conventional type II | Present invention type |
| 4. Adult (pulmonary edema patient) | 46 | 45 | 45 |

In the comparative experiment, common parts for the three assemblies were used. Namely, poly-tetra-fluoro-ethylene having a thickness of 13 μm was used as polymer membrane denoted respectively as 8 in FIG. 1, 8 in FIG. 2 and 8 in FIG. 3, and an aqueous solution containing 0.005 mol of $NaHCO_3$ and 0.02 mol of NaCl was used as electrolye to be retained between the polymer membrane and the glass electrode. Lens paper having a thickness of 40 μm was also used as a spacer between the glass electrode and the polymer membrane for all the assemblies tested. The same temperature of 43.5° C. was used throughout the experiment for heating the assemblies.

As is clear from Table 1, the transcutaneous $CO_2$ measurement assembly of the present invention is far advantageous over the electrode assembly of the conventional type I in respect of the noise level and has extremely smaller drifts and lower noise level compared to even the conventional type II.

As discussed heretofore, the assembly according to the present invention may a) be made smaller and compact in size because it houses the preamplifier within the glass electrode and therefore can be attached to a small area such as on neonatal and premature babies; b) the assembly is free from the noise caused by static coupling and electromagnetic induction because the preamplifier is disposed inside the glass electrode surrounded by the external reference electrode 47 which acts as a shield against the external electromagnetic field; the gain and the offset drift of the preamplifier is extremely reduced because of the exclusion of temperature change of the preamplifier, because of the extremely small temperature changes in the preamplifier. This is because it is placed within the glass electrode maintained at a constant temperature; d) since there exists no liquid inside the glass electrode, the assembly when fallen or inverted by the movement of the patient does not cease functioning though the conventional assemblies do; there is no possibility of the breakage of the glass electrode when the buffere solution freezes in very cold climate. There is no possibility of deterioration of insulation caused by the leakage of the buffer solution of the glass electrode. The mechanical strength of pH responsive glass membrane is increased because the glass electrode is filled with such a solid material as silicone rubber, and it is less susceptible to brokeage.

As heretofore discussed in detail, the present invention definitely improves the disadvantages of the prior art assembly. Although silver deposited membrane was used as a conductive layer in the above embodiment, it is quite possible to form the conductive layer using a conductive paint which contains silver powder. Highly insulating epoxy resin was used for the glass electrode support tube in the above embodiment, but it is naturally possible to substitute it with other insulating members such as glass and ceramic.

What we claim is:

1. In a transcutaneous carbon dioxide measurement electrode assembly having a central tubular glass electrode having a bottom end, said electrode being composed of a highly insulating material, at said bottom end is positioned a pH responsive glass membrane, said glass membrane having an outer surface for contacting the skin and an inner surface exposed to the interior of the tubular glass electrode, a reference electrode surrounding said glass electrode, a membrane holder, carbon dioxide-permeable polymer membrane bonded to said membrane holder and which is positioned at said bottom end, a skin-heating member which provides a body contacting surface and an aperture through which the $CO_2$ gas being measured is carried to said glass electrode via said membrane and further includes a heater for heating the body contacting surface and provided with a heat sensitive element controlling said heater to maintain said body at a designated temperature, said heating member supporting the membrane holder in a space between said reference electrode and said skin heater so as to form between the $CO_2$-permeable membrane and the outer surface of said glass membrane an electrolyte chamber for an electrolyte solution which contacts the reference electrode, the improvement comprising a conductive layer formed on the inner surface of said glass membrane, a preamplifier disposed within said glass electrode, a short lead wire connected between said conductive layer and the input terminal of said preamplifier, the output terminal of said preamplifier adapted to be connected to an external low output impedance, measuring device, said glass electrode being filled with an insulating solid material.

* * * * *